United States Patent [19]

Gallant

[11] 4,174,571

[45] Nov. 20, 1979

[54] METHOD FOR CLEANING TEETH

[75] Inventor: Ben J. Gallant, Portland, Tex.

[73] Assignee: Dentron, Inc., Corpus Christi, Tex.

[21] Appl. No.: 928,907

[22] Filed: Jul. 28, 1978

[51] Int. Cl.² .............................................. A61C 3/06
[52] U.S. Cl. ...................................... 433/216; 433/88
[58] Field of Search ........................ 51/428; 32/58, 59

[56] References Cited

U.S. PATENT DOCUMENTS

| 3,863,628 | 2/1975 | Vit ............................................. 32/58 |
| 3,882,638 | 5/1975 | Black ....................................... 51/428 |
| 3,972,123 | 8/1976 | Black ....................................... 32/58 |

*Primary Examiner*—Robert Peshock
*Attorney, Agent, or Firm*—Kenneth P. Synnestvedt

[57] ABSTRACT

A method for cleaning teeth involving the conjoint use of streams of water and of a water soluble abrasive carried in an air stream.

6 Claims, 2 Drawing Figures

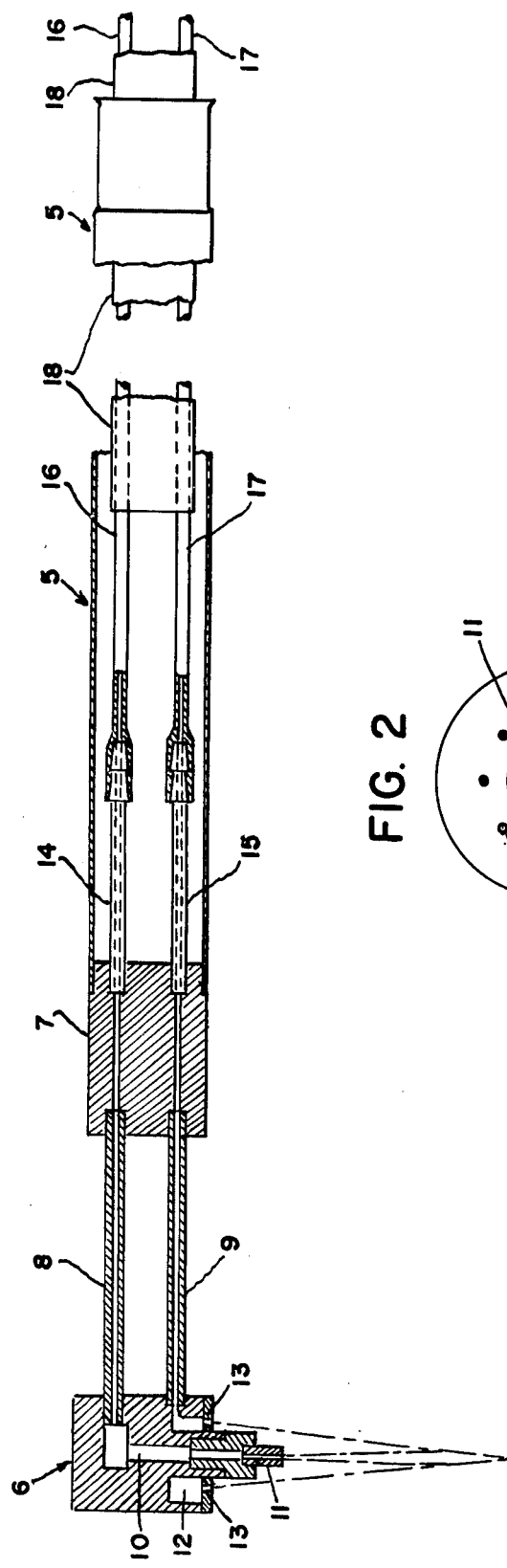
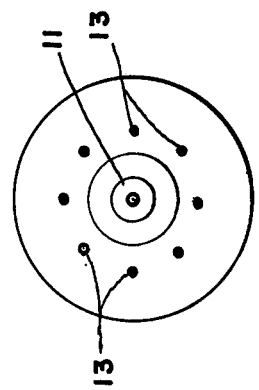
FIG. 1
FIG. 2

METHOD FOR CLEANING TEETH

This invention relates to a method for cleaning teeth and is particularly concerned with cleaning operations involving the use of a powdered abrasive delivered to the surfaces of the teeth to be cleaned by means of a gas stream in which the abrasive particles are suspended.

Tooth cleaning operations of this general type are disclosed, for example, in patents of Robert B. Black, U.S. Pat. Nos. 3,882,638, issued May 13, 1975, and 3,972,123, issued Aug. 3, 1976. As disclosed in said prior patents, the stream of gas, carrying the abrasive particles, is delivered from a handpiece by means of which the abrasive laden stream may be directed to any portion of the tooth surface which it is desired to clean. In addition, as disclosed in said prior patents, provision is made for projection of at least one stream of a liquid, usually water, from the handpiece to the surface of the tooth in an area immediately adjacent to, or even overlapping with the area to which the abrasive stream is directed.

Techniques of the kind just referred to constitute an effective tooth cleaning method, especially for the removal of foreign material from the exposed surfaces of the teeth, such as stain, plaque or even claculus. Stains may originate from various sources, such as tobacco smoking, tobacco chewing, excessive drinking of tea or from vegetable origin. Plaque ordinarily comprises a layer of mucous usually harboring bacteria. Calculus is of several types, especially serumal and salivary, and the calculus deposits tend to accumulate in pockets between the teeth and the surrounding soft tissues. These constituents precipitate and bond themselves to the exposed tooth surfaces.

The method or technique disclosed in the Black patents utilizes various forms of water insoluble abrasive particles for cleaning purposes; and such insoluble particles are effective for the removal of stain, plaque and substantial deposits of calculus. However, such prior technique has certain disadvantages which are overcome in accordance with the method of the present invention, as will be explained herebelow.

In accordance with the present invention, instead of employing water insoluble abrasive particles, it is contemplated to employ water soluble abrasive particles, for instance, sodium bicarbonate. Although it might be expected that the water solubility of the abrasive particles would destroy the cleaning action, suprisingly, this is not the case. Indeed, while the intensity of the abrasion is diminished, so that substantial deposits of calculus may t be removed, I have found that the reduction in intensity of the abrasion is of definite advantage and benefit in the cleaning operation and that notwithstanding the decrease in the intensity of the abrasion, the cleaning action will still be fully effective with respect to stain and plaque, and even with very thin layers of salivary calculus on broad areas of the tooth.

The action referred to above, as provided in accordance with the present invention, occurs to best advantage in the presence of some water on the tooth surface, for instance a film of water such as may be delivered to the surface of the tooth by the water supply means incorporated in the handpiece from which the abrasive stream is also delivered. The powder mixes with the water of the water film as the particles are being dissolved in the water; and during this interval, the abrasive and water form a slurry which effectively and quickly removes stains and plaque, without excessive abrasion of the tooth enamel.

The solubility of the abrasive is also of importance because the water, in effect, "captures" the abrasive, thereby preventing unpleasant dusting within the mouth, and also eliminating any need for applying external vacuum equipment to pick up dust escaping from the mouth.

The abrasive particles may readily be withdrawn from the mouth in solution in the water, as by the normal suction equipment employed by dentists.

Still, further, as compared with the use of insoluble abrasive powder, the employment of the soluble powder eliminates the unpleasant sensation of grit in the patient's mouth; and in addition, the tendency for deposits of such grit in periodontal pockets or below the gingival margin, with possibility of irritation or infection, is eliminated.

Still other advantages and operating characteristics provided for in accordance with the present invention will be developed hereinafter, following a description of the accompanying drawing showing one form of handpiece for developing the abrasive and water streams contemplated for use in accordance with this invention. In the drawing:

FIG. 1 is a view of a handpiece usable in the practice of the invention, with the parts in section so as to illustrate the interior construction, especially of the head of the handpiece; and FIG. 2 is a detail view showing the arrangement of the air-abrasive nozzle and of the surrounding array of water discharge passages used in the handpiece shown.

Referring to FIGS. 1 and 2, the handpiece comprises a tube 5 by which the instrument is to be held when in use in the mouth. The head of the handpiece is generally indicated by the reference numeral 6, and it will be seen that the head is supported at one end of the tube 5 by means of the block 7 and the connected tubes 8 and 9. Tube 8 connects with the central passage 10 in the head which in turn connects with the abrasive nozzle 11 having a discharge passage extended at right angles to the axis of the handle 5.

Tube 9 connects with the annular chamber 12 surrounding the passage 10 and the air-abrasive nozzle, the chamber 12 serving as a supply chamber for the series of water discharge passages 13.

As will be seen from FIGS. 1 and 2, the water discharge passages 13 are arranged in an array surrounding the air-abrasive nozzle 11 and the water passages are preferably inclined somewhat toward the air-abrasive stream. The inclination and spacing between the central air-abrasive stream and the water streams should be such as to provide for impingement of both the abrasive and the water on the tooth surface in areas close to or even overlapping each other.

It will be seen that in the handpiece shown in the drawing, the air-abrasive and water nozzle arrangement is capable of providing a curtain or envelope of water surrounding but spaced from the ari-abrasive stream in the target area of the air-abrasive stream. At the same time, the envelope or curtain of water will merge with the air-abrasive stream in the region of or beyond the normal air-abrasive target distance from the head of the handpiece.

The block 7 at the end of the handle 5 is provided with passages which interconnect the tubes 8 and 9 with tubes 14 and 15 adapted to cooperate with the flexible supply tubes 16 and 17 for the air-abrasive and water, these flexible tubes 16 and 17 desirably being confined within a common sheath indicated at 18. The flexible tubes 16 and 17 are, of course, extended to supply and control equipment, for instance, of the type shown in the U.S. patents to Robert B. Black above identified.

It will be understood that equipment of various types may be employed in the practice of the invention; but in general, the equipment should provide for the establishment of a stream of water closely adjacent to a stream of abrasive laden gas, preferably air. It is also of advantage that the water and abrasive streams be directed from spaced but closely adjacent points and further that the streams converge. The angle of convergence is preferably such that the paths of the streams intersect at a point spaced from the delivery orifices at a point sufficiently close to the delivery orifices, so that in the manual use of the handpiece within the mouth of a patient, there would be minimal opportunity for the abrasive stream by itself to strike any tissues within the mouth. For example, if the point of intersection of the paths is less than about one inch from the orifices, there would be minimal opportunity for the abrasive stream alone to strike the tissues when the handpiece is introduced into or withdrawn from the mouth.

It should be understood that convergence of the two streams is not an essential in the practice of the invention, because any arrangement which will bring the stream of water and the stream of abrasive laden air to the surface of the tooth to be cleaned, with the two streams close to each other at the point of impact on the tooth, will enable the cleaning action to occur under the condition contemplated, i.e., the condition in which some water is present, preferably a film of water, on the tooth surface against which the abrasive stream is directed. In this way, the soluble abrasive particles will be in the process of dissolving in the water at the point of impact of the abrasive stream; and this gives the desired "gentle" abrasive action desired for the removal of most types of stain or plaque, such as the calculus above referred to.

By providing this "gentle" abrasive action, the intensity of the abrasion may be kept at a level which will avoid adversely affecting the tooth enamel.

As will be understood, the various materials to be cleaned from the tooth may require some variation in the intensity of the abrasive action, and this variation in intensity may be provided by alterating the distance of the delivery orifices from the tooth. The provision for generation of the two streams in spaced relation to each other and on paths which converge is also of importance in providing for variation in the intensity of the abrasion. If the jets are delivered to the tooth at very close range from the orifices, it is possible to provide for direct impingement of the abrasive laden air substantially independently of the water stream, in which event the abrasion will be more intense; but if the jets are delivered to the tooth from a greater distance, then the convergence of the streams will cause the water to be present at the point of impact of the abrasive laden air stream.

As above indicated, for most purposes, it is contemplated that the method be carried out in a manner to provide for some water film on the surface of the tooth to which the abrasive stream is directed, thereby providing a condition in which a slurry of the abrasive and water is formed on the area to be cleaned, and the continued impingement of the abrasive stream on the slurry will cause the desired intensity of abrasive action as the abrasive particles are being dissolved in the water present.

For most purposes, it is contemplated that the abrasive comprise particles of sodium bicarbonate, but certain other water soluble materials may also be employed in powdered form, for instance sodium glutamate, or sodium gluconate. Although the particle size is not critical, it is preferred for most purposes to employ screened particles of size in the range from about 140 to 200 mesh.

Although gases other than air may be employed in establishing the abrasive stream, air is the preferred gas for the purpose. It is also possible to employ a liquid other than water, but the technique of the invention requires that the abrasive and the liquid be selected so that the abrasive is soluble in the liquid. Water is preferred for use in the mouth. The quantity of water is most desirably just sufficient to dissolve the quantity of abrasive being delivered.

I claim:

1. A method for cleaning teeth comprising concurrently directing separate streams of water and of an abrasive laden gas against a tooth to be cleaned, the abrasive comprising particles of a water soluble material, and the water and gas streams being directed in predetermined relation to each other and to areas of the tooth immediately adjacent to each other.

2. A method as defined in claim 1 in which the abrasive is sodium bicarbonate.

3. A method as defined in claims 1 or 2 in which a plurality of streams of water are concurrently directed against the tooth to be cleaned, the streams of water being directed in predetermined paths surrounding the abrasive laden gas stream.

4. A method as defined in claim 1 in which the quantity of water delivered to the surface of the tooth is sufficient to dissolve the abrasive particles delivered to the surface of the tooth by said gas stream.

5. A method for cleaning teeth comprising directing a stream of an abrasive laden gas against a tooth surface in the presence of a film of water on said surface, the abrasive comprising particles of water soluble abrasive material, and replenishing the water film at a rate sufficient to dissolve the abrasive particles delivered to the tooth surface by said stream.

6. A method for cleaning teeth comprising directing a stream of an abrasive-laden gas toward the surface of a tooth to be cleaned, concurrently directing a stream of water toward said surface, the abrasive comprising particles of a water-soluble material, and the water and gas streams being directed to provide for the presence of both water and abrasive particles within the same target area of the tooth surface to be cleaned.

* * * * *